United States Patent
Moon et al.

(10) Patent No.: US 10,064,778 B2
(45) Date of Patent: Sep. 4, 2018

(54) WALKING ASSISTANCE DEVICES AND METHODS OF CONTROLLING THE SAME

(71) Applicant: Samsung Electronics Co., Ltd., Suwon-Si, Gyeonggi-Do (KR)

(72) Inventors: Kyung-Won Moon, Yongin-si (KR); Ji Young Kim, Anyang-si (KR); Young-Bo Shim, Seoul (KR); Bok Man Lim, Yongin-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 1061 days.

(21) Appl. No.: 14/337,684

(22) Filed: Jul. 22, 2014

(65) Prior Publication Data

US 2015/0094823 A1    Apr. 2, 2015

(30) Foreign Application Priority Data

Oct. 2, 2013 (KR) .................... 10-2013-0117893

(51) Int. Cl.
  *A61H 1/02*    (2006.01)
  *A61H 3/00*    (2006.01)
  (Continued)

(52) U.S. Cl.
  CPC ............. *A61H 3/00* (2013.01); *A61B 5/1038* (2013.01); *A61B 5/112* (2013.01); *A61H 1/0244* (2013.01); *A61H 1/024* (2013.01); *A61H 1/0266* (2013.01); *A61H 2201/1215* (2013.01); *A61H 2201/1238* (2013.01); *A61H 2201/164* (2013.01); *A61H 2201/1676* (2013.01); *A61H 2201/50* (2013.01);
  (Continued)

(58) Field of Classification Search
  CPC .......... A61H 1/00; A61H 1/02; A61H 1/0214; A61H 1/0237; A61H 1/024; A61H 1/0244; A61H 2001/0248; A61H 1/0262
  See application file for complete search history.

(56) References Cited

U.S. PATENT DOCUMENTS

| | | | |
|---|---|---|---|
| 8,849,457 B2 * | 9/2014 | Jacobsen ............... | A61H 3/008 623/24 |
| 2005/0258210 A1 * | 11/2005 | Chu ........................ | A45F 3/08 224/637 |

(Continued)

FOREIGN PATENT DOCUMENTS

| JP | 2002301124 A | 10/2002 |
|---|---|---|
| JP | 2011229568 A | 11/2011 |

(Continued)

*Primary Examiner* — Michael Tsai
(74) *Attorney, Agent, or Firm* — Harness, Dickey & Pierce, P.L.C.

(57) ABSTRACT

A walking assistance device may include at least one walking assistance unit configured to assist a user in walking; and/or a controller configured to control, based on a walk pattern of the user, the at least one walking assistance unit to produce torque only in at least one assistance period needing walking assistance in a walk cycle. A method of controlling walking assistance may include: calculating a walking assistance time using a difference between a start time and a termination time of an assistance period needing the walking assistance in a walk pattern; and/or assisting a user in walking when the assistance period begins, by producing torque for the walking assistance time.

16 Claims, 9 Drawing Sheets

(51) Int. Cl.
*A61B 5/103* (2006.01)
*A61B 5/11* (2006.01)

(52) U.S. Cl.
CPC .......... *A61H 2201/5007* (2013.01); *A61H 2201/5012* (2013.01); *A61H 2201/5061* (2013.01); *A61H 2201/5069* (2013.01); *A61H 2201/5092* (2013.01)

(56) References Cited

U.S. PATENT DOCUMENTS

| | | | |
|---|---|---|---|
| 2006/0270951 A1* | 11/2006 | Ikeuchi | A61H 3/00 601/5 |
| 2008/0139968 A1* | 6/2008 | Endo | A61B 5/04888 600/595 |
| 2009/0131839 A1 | 5/2009 | Yasuhara | |
| 2010/0271051 A1 | 10/2010 | Sankai et al. | |
| 2012/0310122 A1 | 12/2012 | Endo et al. | |
| 2014/0212243 A1* | 7/2014 | Yagi | A61H 3/00 414/2 |
| 2014/0358053 A1* | 12/2014 | Triolo | A61H 3/00 602/16 |

FOREIGN PATENT DOCUMENTS

| | | |
|---|---|---|
| JP | 2013094502 A | 5/2013 |
| JP | 2013111368 A | 6/2013 |

* cited by examiner

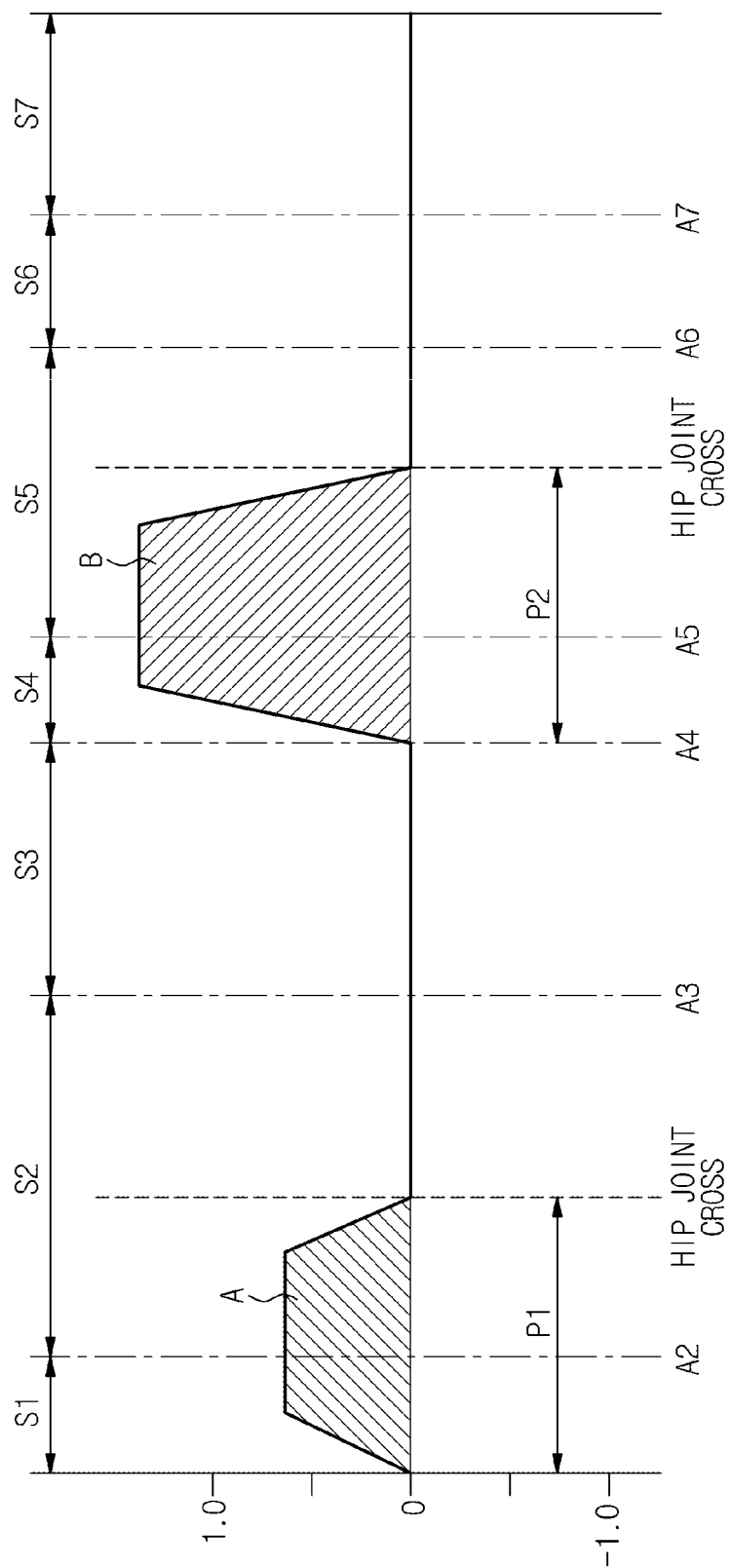

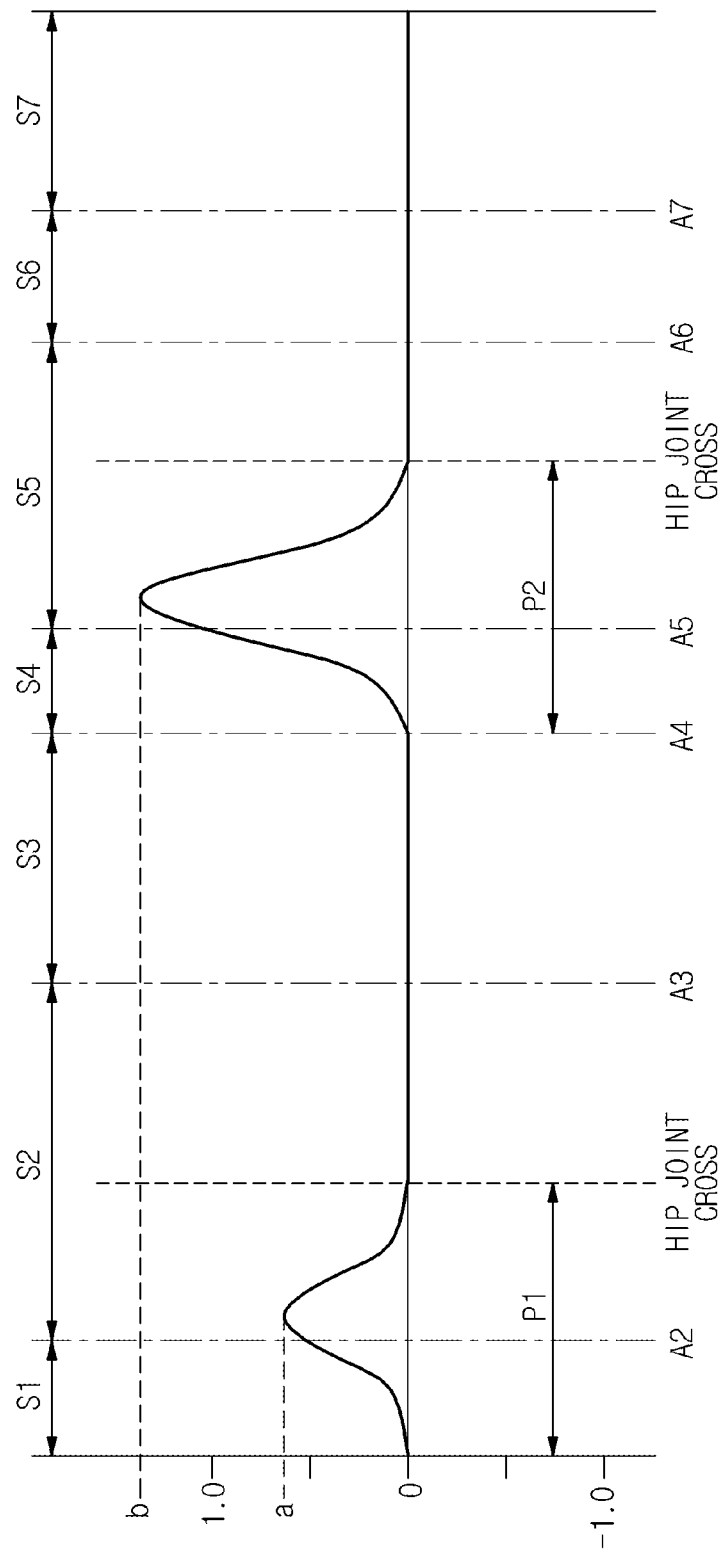

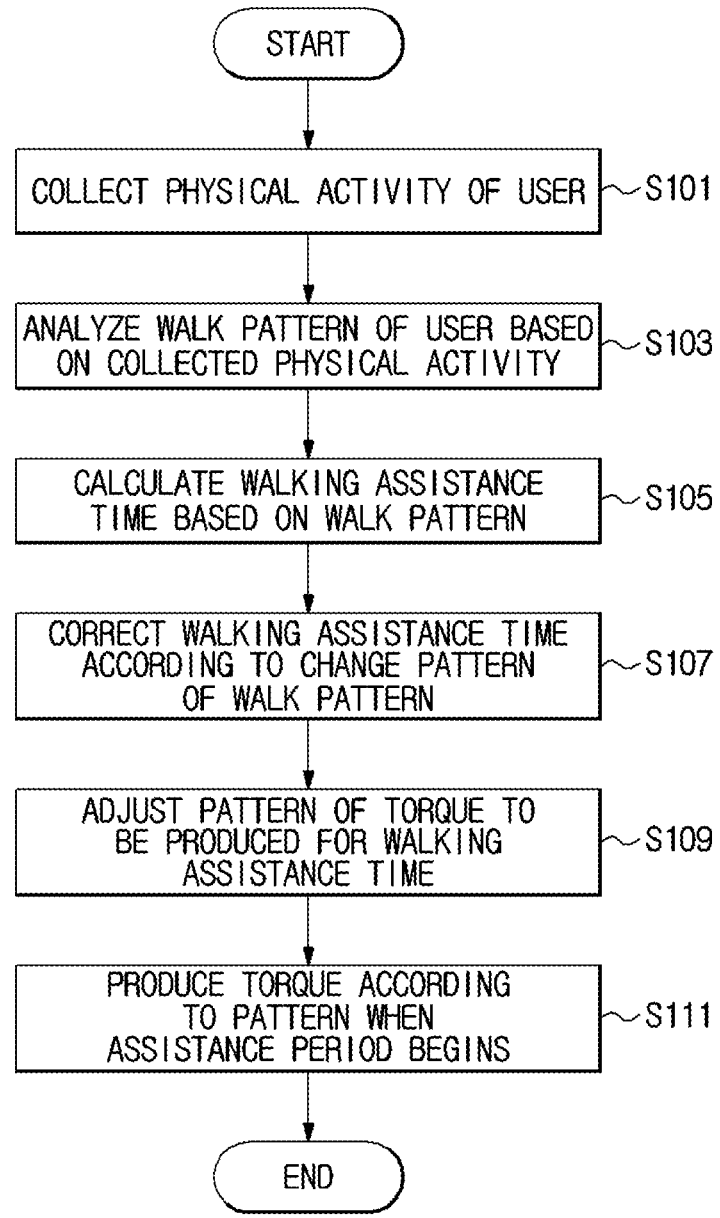

WALKING ASSISTANCE DEVICES AND METHODS OF CONTROLLING THE SAME

CROSS-REFERENCE TO RELATED APPLICATION(S)

This application claims priority from Korean Patent Application No. 10-2013-0117893, filed on Oct. 2, 2013, in the Korean Intellectual Property Office (KIPO), the entire contents of which are incorporated herein by reference.

BACKGROUND

1. Field

Some example embodiments may relate to walking assistance devices that assists a user in walking and/or methods of controlling the same.

2. Description of Related Art

Research has been actively conducted into assistive robots that augment human actions. Assistive robots may be used for various purposes in such fields as military, industry, rehabilitation, and/or welfare.

Particularly, walking assistance devices have been developed and/or used for physical therapy or rehabilitation training. The walking assistance device may be a device to assist a user in walking by operating a walking assistance unit.

In addition, with the rise of the elderly population, the walking assistance device may be increasingly used not only for physical therapy and rehabilitation training, but also to assist the old whose muscular strength is weakened or to increase physical strength.

In general, wearable robots to assist muscular strength may include a lower extremity muscular strength assistance robot for behavior of lower extremities. Among these wearable robots, the lower extremity muscular strength assistance robot denotes a robot serving to assist force of wearer's legs to assist walking using human-robot synchronization.

Such a lower extremity muscular strength assistance robot may be driven so as to sense a wearer's intention to walk and to assist corresponding muscular strength. Here, sensing of the wearer's intention to walk may mean sensing of a wearer's intention to start walk or to finish walk, or mean sensing of moving states of the left foot and the right foot.

Although some example embodiments will be described with relation to wearable robots for humans and control methods thereof, those skilled in the art will appreciate that some example embodiments may be applied to other types of robots, systems, and control methods, such as wearable robots for animals and control methods thereof, or more general purpose systems and control methods.

SUMMARY

Some example embodiments may provide walking assistance devices that assist users wearing the same according to walk patterns of the users only in walking sections in which walking needs to be assisted.

Some example embodiments may provide methods of controlling walking assistance devices that assist users wearing the same according to walk patterns of the users only in walking sections in which walking needs to be assisted.

In some example embodiments, a walking assistance device may comprise: at least one walking assistance unit configured to assist a user in walking; and/or a controller configured to control, based on a walk pattern of the user, the at least one walking assistance unit to produce torque only in at least one assistance period needing walking assistance in a walk cycle.

In some example embodiments, the controller may be further configured to calculate a walking assistance time using a difference between a start time and a termination time of the at least one assistance period. The controller may be further configured to control the at least one walking assistance unit to produce the torque for the calculated walking assistance time when the at least one assistance period starts.

In some example embodiments, the torque may be produced to gradually increase and then gradually decrease.

In some example embodiments, the at least one assistance period may be a period in the walk cycle during which energy consumption is higher than an average energy consumption in the walk cycle.

In some example embodiments, the at least one assistance period may comprise a weight shift period and a mass shift period. The weight shift period may begin when one foot of the user contacts a ground surface and terminates when hip joints of the user cross each other. The mass shift period may begin when the other foot of the user contacts the ground surface and terminates when the hip joints of the user cross each other.

In some example embodiments, when the walk cycle includes a plurality of assistance periods of the at least one assistance period, a first torque pattern produced during a portion of the plurality of assistance periods may differ from a second torque pattern produced during the other portion of the plurality of assistance periods.

In some example embodiments, the walking assistance device may further comprise: a status collector configured to collect a physical activity of the user. The controller may comprise a pattern analysis unit configured to analyze the walk pattern of the user based on the collected physical activity.

In some example embodiments, the status collector may comprise a pressure sensor configured to sense change in pressure applied to feet of the user.

In some example embodiments, the status collector may comprise an encoder sensor configured to collect information related to rotation of the at least one walking assistance unit.

In some example embodiments, the controller may comprise a pattern analysis unit configured to correct the walking assistance time based on a change pattern of the walk pattern of the user.

In some example embodiments, the controller may comprise a torque adjustment unit configured to adjust a pattern of torque to be produced by the walking assistance unit, based on the at least one walking assistance time.

In some example embodiments, a method of controlling walking assistance may comprise: calculating a walking assistance time using a difference between a start time and a termination time of an assistance period needing the walking assistance in a walk pattern; and/or assisting a user in walking when the assistance period begins, by producing torque for the walking assistance time.

In some example embodiments, the method may further comprise: collecting a physical activity of the user; and/or analyzing the walk pattern of the user based on the collected physical activity.

In some example embodiments, in the assisting the user in walking, the torque produced may be gradually changed.

In some example embodiments, the calculating of the walking assistance time may comprise correcting the calculated walking assistance time based on a change pattern of the walk pattern of the user.

In some example embodiments, the assisting the user in walking may comprise adjusting a pattern of the torque produced based on the calculated walking assistance time.

In some example embodiments, the assisting the user in walking may comprise gradually increasing the torque produced and gradually decreasing the torque produced.

In some example embodiments, the assistance period may comprise a weight shift period and a mass shift period. The weight shift period may begin when one foot of the user contacts a ground surface and terminates when hip joints of the user cross each other. The mass shift period may begin when the other foot contacts the ground surface and terminates when the hip joints cross each other.

In some example embodiments, in the calculating of the walking assistance time, a time of the weight shift period and a time of the mass shift period may be calculated. In the assisting the user in walking, the torque may be produced for the time of the weight shift period when the weight shift period begins, and the torque may be produced for the time of the mass shift period when the mass shift period begins.

BRIEF DESCRIPTION OF THE DRAWINGS

The above and/or other aspects and advantages will become more apparent and more readily appreciated from the following detailed description of example embodiments, taken in conjunction with the accompanying drawings, in which:

FIGS. 7A and 7B are graphs depicting an example of torque produced by the walking assistance unit; and FIG. 8 is a flowchart illustrating a method of controlling a walking assistance device according to some example embodiments.

DETAILED DESCRIPTION

Figure 1:
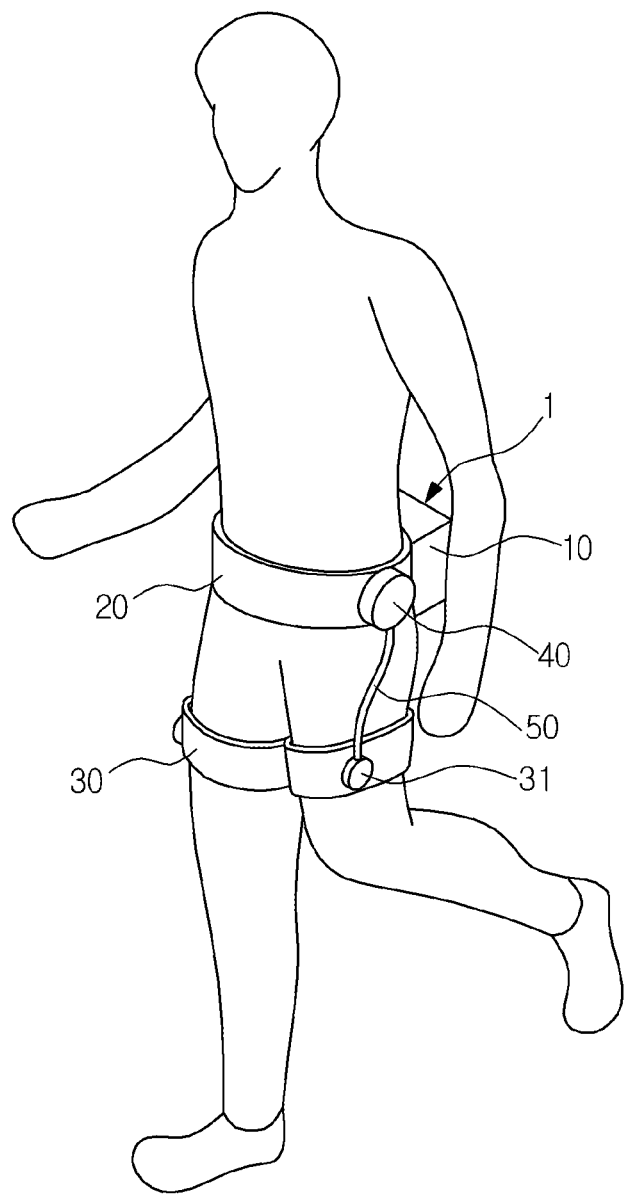
FIG. 1 is a perspective view illustrating a walking assistance device according to some example embodiments.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIG. 1 is a perspective view illustrating a walking assistance device according to some example embodiments.

Referring to FIG. 1, a walking assistance device 1 includes a body 10, a waist fixing part 20, a leg fixing part 30, a joint part 40, and a transmission member 50.

The body 10 is arranged at a portion of the waist fixing part 20. A walking assistance unit, a battery, or various circuits necessary for control of the walking assistance device 1 may be mounted in the body 10.

The waist fixing part 20 of the walking assistance device 1 is fixed to the waist of the user wearing the walking assistance device 1. In some example embodiments, the waist fixing part 20 may have a portion for fixation. For example, one end of the waist fixing part 20 may be provided with a tightening part in the form of a belt. The waist fixing part 20 may be formed of an elastic material such as rubber.

The leg fixing part 30 fixes the walking assistance device 1 to the femoral region of the user. In some example embodiments, the leg fixing part 30 may have a portion for fixation. For example, one end of the leg fixing part 30 may be provided with a tightening part in the form of a belt. The leg fixing part 30 may be formed of an elastic material such as rubber. One surface of the leg fixing part 30 may be provided with a fixing part 31 to be coupled to a transmission member 50.

The joint part 40 may be arranged at one side of the waist fixing part 20. The joint part 40 may be structured to rotate by receiving torque from the walking assistance unit provided in the body 10. In some example embodiments, a plurality of joint parts 40 may be provided. The transmission member 50 may be coupled to a portion of the joint part 40. Accordingly, when the joint part 40 rotates, the transmission member 50 also rotates.

One end of the transmission member 50 is coupled to the joint part 40, and the other end thereof is coupled to the fixing part 31. Accordingly, the transmission member 50 rotates along with rotation of the joint part 40. As the transmission member 50 rotates, torque is transmitted to the fixing part 31, and thereby the leg fixing part 30 also rotates.

In other words, when the joint part 40 rotates with torque received from the walking assistance unit, torque is in turn transmitted to the transmission member 50 and the leg fixing part 30 coupled to the joint part 40. Accordingly, the torque produced by the walking assistance device 1 is transmitted to the femoral region of the user, assisting the user in walking.

While the walking assistance device 1 is illustrated in FIG. 1 as assisting only the hip joint, it should be understood that the walking assistance device 1 is also applicable to the knee joint and the ankle joint.

Hereinafter, a detailed description will be given of a walking assistance device with reference to FIGS. 2 to 7.

Figure 2:
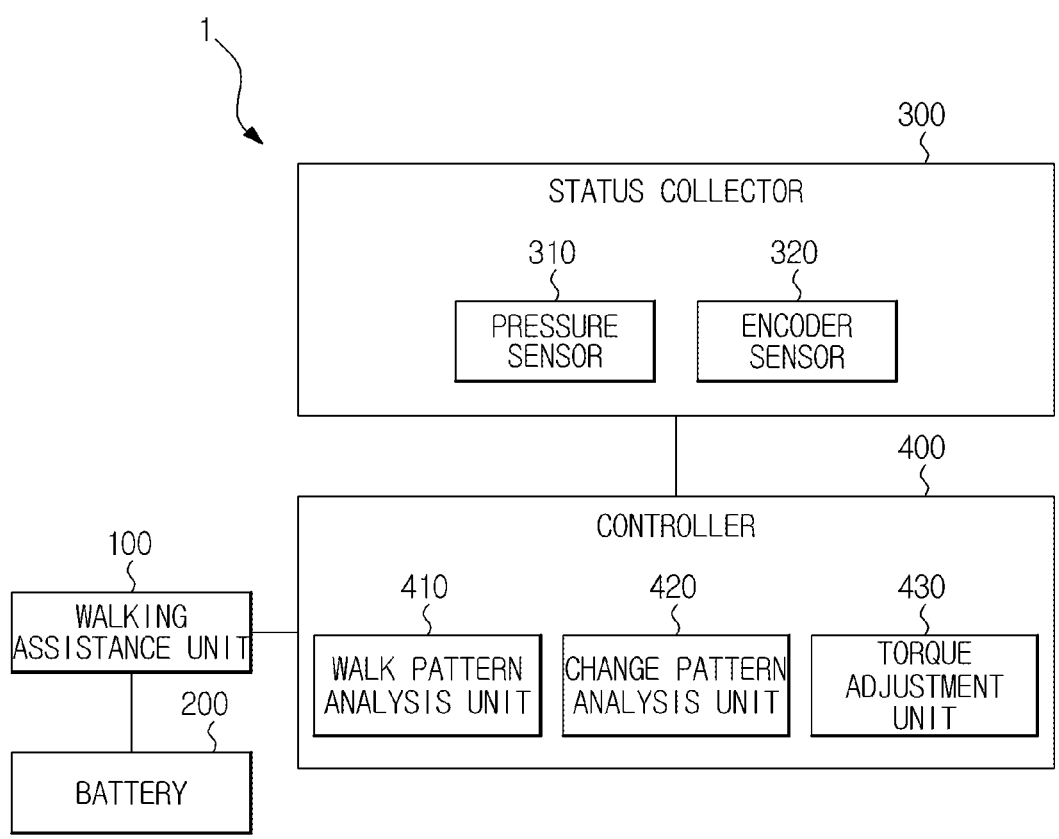
FIG. 2 is a control block diagram illustrating a walking assistance device according to some example embodiments.

FIG. 2 is a control block diagram illustrating a walking assistance device according to some example embodiments.

Figure 3:
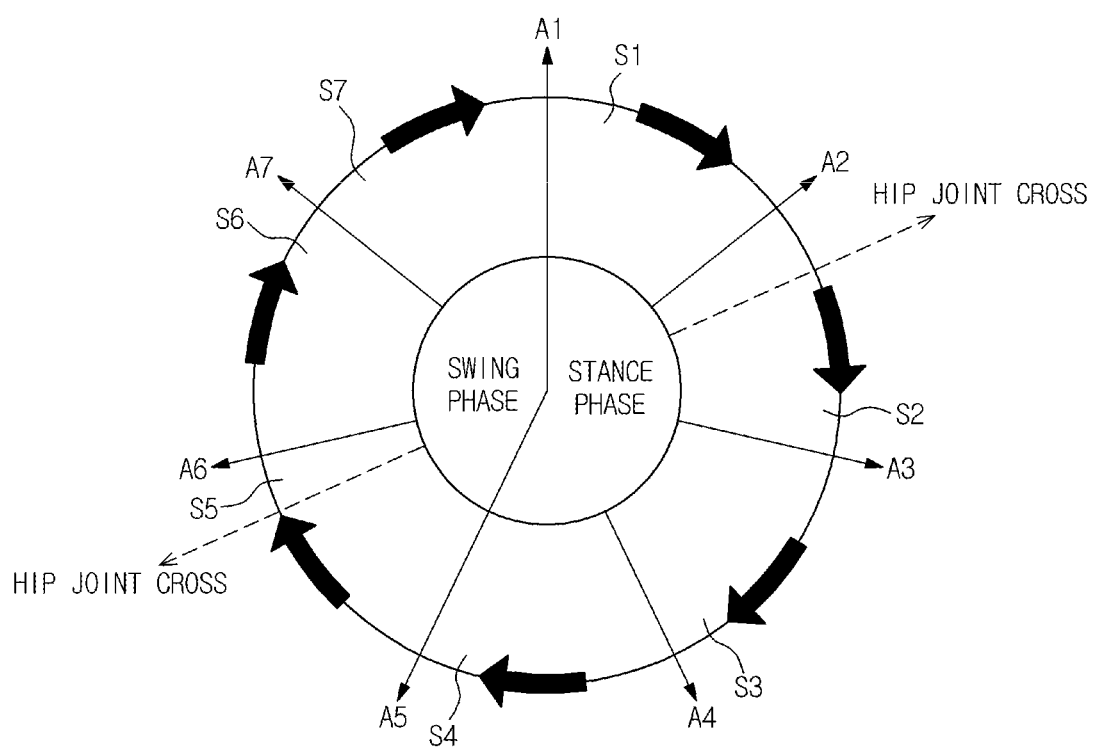
FIG. 3 is a view illustrating a walk pattern.

FIG. 3 is a view illustrating a walk pattern.

Figure 4:
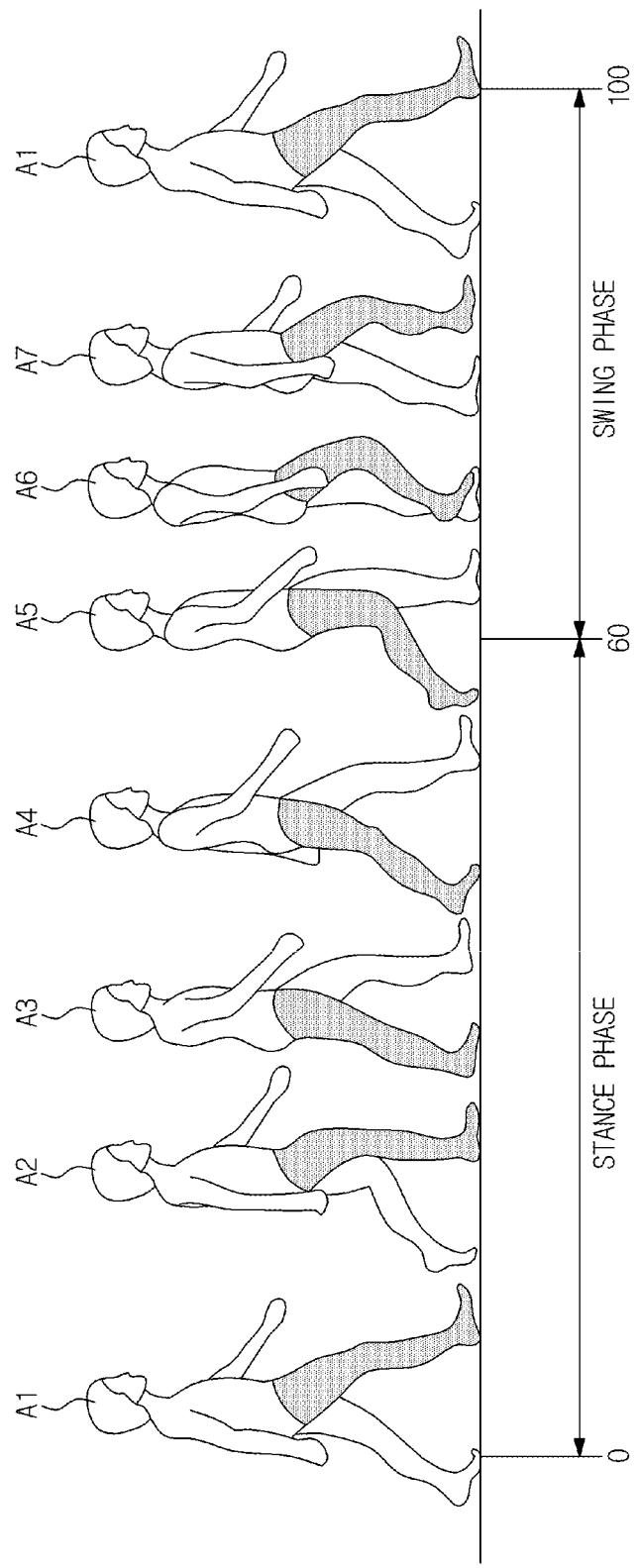
FIG. 4 is a view illustrating continuous walking poses at each phase to describe the walk pattern in detail.

FIG. 4 is a view illustrating continuous walking poses at each phase to describe the walk pattern in detail.

Figure 5:
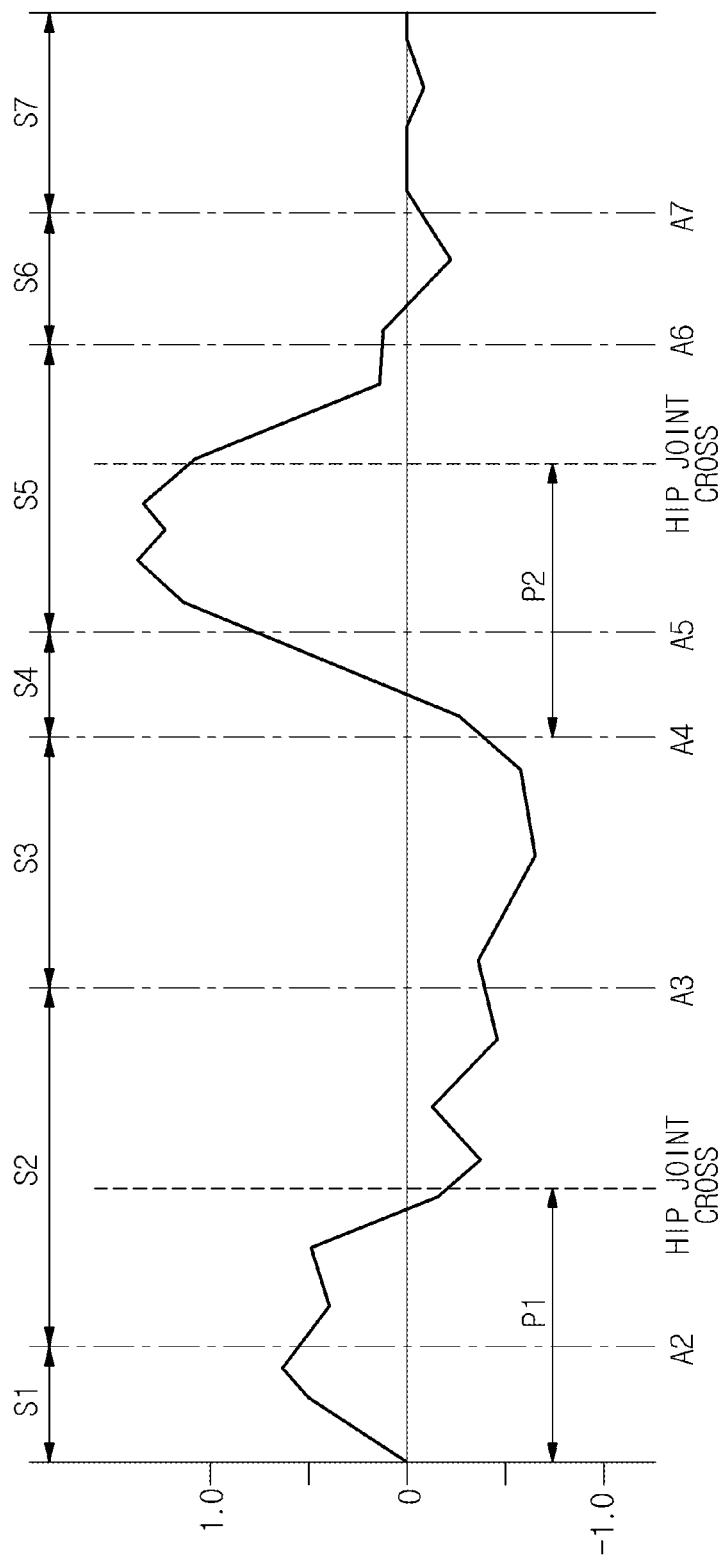
FIG. 5 is a graph depicting an example of energy necessary for walking.

FIG. 5 is a graph depicting an example of energy necessary for walking.

Figure 6:
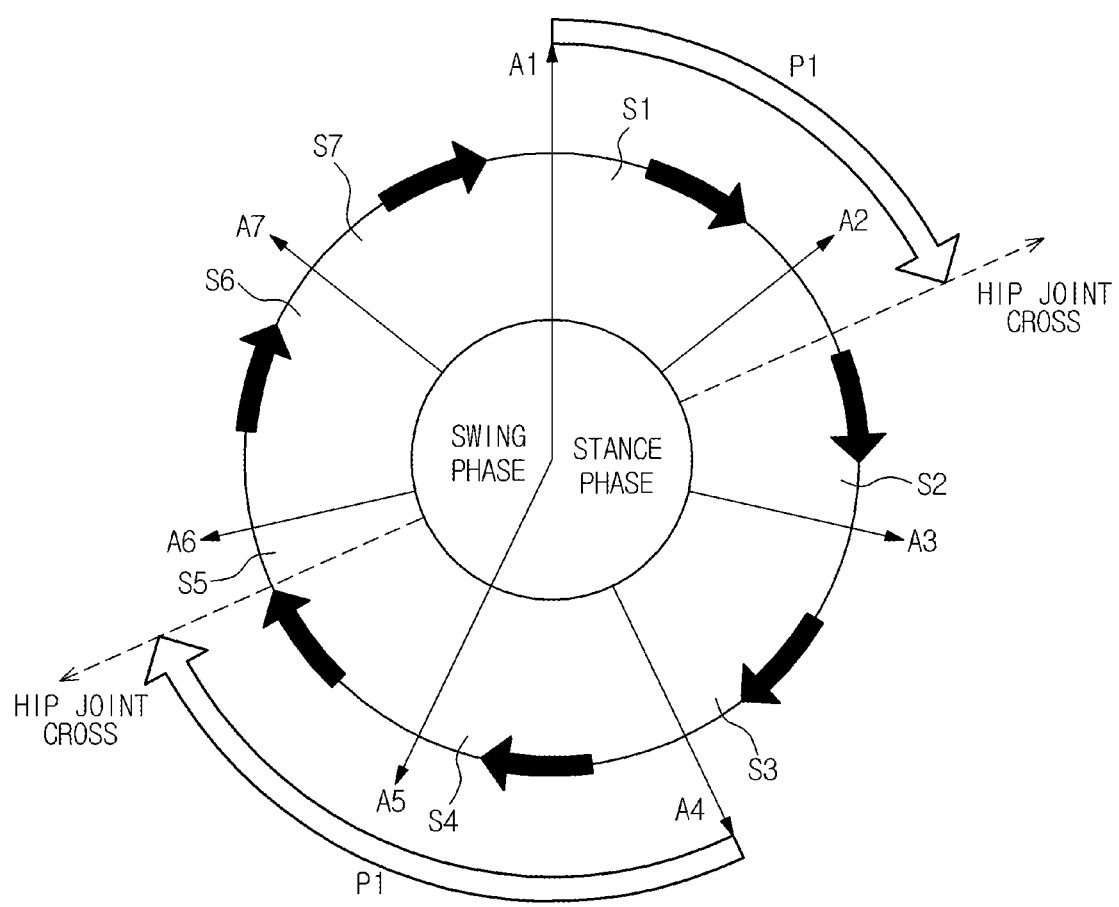
FIG. 6 is a view illustrating an example of an assistance period in the walk pattern in which walking assistance occurs.

FIG. 6 is a view illustrating an example of an assistance period in the walk pattern in which walking assistance occurs.

FIG. 7 is a graph depicting an example of torque produced by the walking assistance unit.

Referring to FIG. 2, the walking assistance device 1 includes a walking assistance unit 100, a battery 200, a status collector 300, and a controller 400.

The walking assistance unit 100 produces torque according to control by the controller 400, thereby assisting the user wearing the walking assistance device 1 in walking. In some example embodiments, the walking assistance unit 100 may be an actuator such as an electric motor or a hydraulic motor. In addition, the torque may follow a pattern of gradually increasing and then gradually decreasing.

The walking assistance device 1 may include a plurality of walking assistance units 100. For example, the walking assistance units 100 may be provided to joints of the legs to assist the user in walking.

The battery 200 may supply electricity to the walking assistance unit 100, allowing the walking assistance unit 100 to produce torque. In some example embodiments, the battery 200 may be a primary cell or a secondary cell reusable though recharge. For example, the battery 200 may be a lithium cell or a rechargeable lithium polymer battery.

The status collector 300 collects physical activities of the user. In some example embodiments, the physical activities refer to various activities related to a walk pattern of the user. Hereinafter, a detailed description will be given of a walk cycle or walk pattern with reference to FIGS. 3 and 4.

Walking has a specific periodicity. More specifically, when walking, a user repeats physical activities in the same order. A period from the time one leg contacts the ground to the time the leg contacts the ground again is referred to as the walk cycle. A walk pattern of the user may be collected through the physical activities collected during repetition of the walk cycle performed by the user.

Referring to FIGS. 3 and 4, the walk cycle refers to a period from the time the heel of one leg contacts the ground to the time the heel contacts the ground again. Based on whether the sole of the user's foot contacts the ground, the walk cycle may be divided into a stance phase and a swing phase. The stance phase is a period during which the sole of the user's foot contacts the ground. The stance phase accounts for about 60% of the walk cycle. The swing phase is a time during which the sole is separated from the ground. The swing phase accounts for about 40% of the walk cycle.

The stance phase includes loading response S1, midstance S2, terminal stance S3, and pre-swing S4. The swing phase includes initial swing S5, midswing S6, and terminal swing S7.

More specifically, the loading response S1 begins with initial contact of the sole of one leg with the ground at A1. During the loading response S1, the user's weight moves forward as the sole of one foot contacts the ground. The knee joint of the leg is slightly folded to absorb shock according to shift of the weight. In addition, according to shift of the weight, the foot of the other leg leaves the ground.

When the toes of the other leg leave the ground at A2, the loading response S1 is terminated and the midstance S2 begins. During the midstance S2, the center of mass of the body is aligned with the center of the foot of one leg. At this time, the hip joint of this leg changes from a folded position to the unfolded position, and the ankle joint of the other leg pulls the instep of the foot upward. Meanwhile, as the hip joint of one leg is unfolded, hip joint cross occurs between the hip, and the heel of the leg begins to leave the ground.

When the heel of one leg leaves the ground at A3, the midstance S2 is terminated and the terminal stance S3 begins. During the terminal stance S3, the hip joint and the knee joint of one leg maintain the unfolded positions, while the heel of the other leg prepares to contact the floor.

When the heel of the other leg contacts the ground at A4, the terminal stance S3 is terminated and the pre-swing S4 begins. In pre-swing S4, the toes of one leg begin to leave the ground. At this time, the hip joint and the knee joint of this leg are gradually folded.

As the toes of one leg leave the ground at A5, the pre-swing S4 is terminated and the initial swing S5 begins. During the initial swing S5, one leg swings in the air. The swing speed of the leg gradually increases. In addition, hip joint cross occurs between both hip joints during the initial swing S5.

When both feet come to positions adjacent to each other at A6, the initial swing S5 is terminated and the midswing S6 begins. The midswing S6 is a deceleration phase. During the midswing S6, the hip joint and the knee joint of one leg are gradually unfolded, crossing the central line of the body.

When the tibia is vertical at A7, the midswing S6 is terminated and the terminal swing S7 begins. During the terminal swing S7, the heel of one leg prepares to contact the ground again. At this time, the hip joint of this leg maintains a slightly folded position, and the knee joint of this leg is fully unfolded.

When the heel of one leg contacts the ground again at A8, the terminal swing S7 is terminated and the loading response S1 begins again.

The respective phases of the walk cycle essentially occur. The walk cycle may vary to some extent in the user's walking. For example, the period of the walk cycle or the ratio of each phase in the walk cycle may vary to some extent according to personal factors of the user such as the walking speed and walking habit.

A walk cycle reflecting personal factors of the user as above is referred to as a walk pattern. The walk pattern may be produced according to specific and individual physical activities collected based on the aforementioned walk cycle. Accordingly, the walk pattern may vary as the walk cycle proceeds, and may also vary among users.

By assisting a user in walking based on a walk pattern produced by collecting the physical activities that occur specifically and individually, the efficiency of walking assistance may be increased, and feeling of difference caused to the user by the device may be minimized.

Again referring to FIG. 4, the status collector 300 collects physical activities of the user to analyze the walk pattern. That is, the status collector 300 collects physical activities such as contact between the feet and the ground or the hip joint cross that occurs in the walk cycle. The collected physical activities are used to analyze the walk pattern.

In addition, the status collector 300 may include a pressure sensor 310. In some example embodiments, the pressure sensor 310 refers to a sensor that senses change of pressure applied to the feet. More specifically, the status collector 300 may include a plurality of pressure sensors 310. In this case, the pressure sensors 310 may be positioned at the front and back of the feet. Based on the change of pressure sensed through the pressure sensor 310, information about physical activities, such as contact or spacing between the toes and heel and the ground, may be collected.

In addition, the status collector 300 may include an encoder sensor 320. In some example embodiments, the encoder sensor 320 may measure the rotational angle or rotation rate of the walking assistance unit 100. More specifically, the encoder sensor 320 may measure the rotational angle or rotation rate of the walking assistance unit 100, thereby collecting information about physical activities such as folded angle of a joint and crossing of both joints.

The controller 400 controls assisted walking by the walking assistance unit 100 based on the walk pattern. More specifically, the controller 400 controls the walking assistance unit 100 based on the user's walk pattern such that the walking assistance unit 100 produces torque only in the assistance period in the walk cycle.

In some example embodiments, the assistance period is a section of walking in which walking needs to be assisted. More specifically, the assistance period is a section in which a relatively large amount of energy is consumed in the walk cycle. Hereinafter, the assistance period will be described in detail with reference to FIGS. 4 to 6.

Referring to FIGS. 4, 5, and 6, once the loading response S1 begins with contact of the heel of one leg with the ground, energy is necessary for this leg to move the body weight in the travel direction from the loading response S1 until the point in the midstance S2 at which the hip joints cross each other.

Thereafter, from the time at which the hip joints cross each other, energy is consumed for braking of this leg in the opposite direction.

Meanwhile, as the pre-swing S4 begins with contact of the heel of the other leg with the ground, the one leg is swung in the travel direction. At this time, energy for swinging the one leg is needed from the time of the pre-swing S4 at which swinging of the leg begins until the hip joints cross each other.

After the hip joints cross each other, some energy is consumed to brake one leg in the opposite direction.

Accordingly, sections in which a relatively large amount of energy is consumed in the walk cycle, such as a weight shift period P1, in which shift of the body weight occurs, and a mass shift period P2, in which shift of a mass of a leg occurs, may be set to the assistance period. In some example embodiments, the weight shift period P1 begins at the time at which the heel of one leg contacts the ground and ends at the time at which the hip joints cross each other. The weight shift period P1 is a section in which one leg needs energy to shift the body weight. The mass shift period P2 begins at the time the heel of the other leg contacts the ground and ends at the time the hip joints cross each other. The mass shift period P2 is a section in which energy is needed for one leg to swing in the travel direction.

Hereinafter, the assistance period will be assumed to be the weight shift period P1 and the mass shift period P2. The weight shift period P1 and the mass shift period P2 are merely a representative example of a walking section in which assisted walking is necessary, and the assistance period should not be construed as being limited to the weight shift period P1 or the mass shift period P2. The assistance period should be construed as including all sections in the walk pattern in which a relatively large amount of energy is consumed and thus the assisted walking device needs to produce torque.

By determining the time for the assistance period according to the user's walk pattern, feeling of difference caused to the user by the device may be minimized. In addition, the walking assistance device may properly assist the user in walking even when the user changes pace and thus the time for the assistance period changes. Moreover, in walking, by assisting the user only in the assistance period in which a relatively large amount of energy is consumed, consumption of battery power of the battery 200 may be minimized.

More specifically, once the assistance period begins, the controller 400 controls the walking assistance unit 100 to produce torque for the time of walking assistance. In some example embodiments, the time of walking assistance may be calculated using difference between the start time of the assistance period and the termination time of the assistance period in the walk pattern.

For example, the controller 400 may calculate the time of walking assistance in the weight shift period P1 using the time difference between the time at which the heel of one leg contacts the ground and the time the hip joints cross each other, and may calculate the time of walking assistance in the mass shift period P2 using the time difference between the time at which the heel of one leg contacts the ground and the time at which the hip joints cross each other.

In addition, the controller 400 may sense start of the assistance period based on the physical activities collected by the status collector 300. When start of the assistance period is sensed, the controller 400 may produce torque for the calculated walking assistance time.

The controller 400 may include a walk pattern analysis unit 410. In some example embodiments, the walk pattern analysis unit 410 analyzes the user's walk pattern based on the physical activities collected by the status collector 300. More specifically, the walk pattern analysis unit 410 may analyze the walk pattern by matching physical activities collected by the status collector 300 in real time to the walk cycle.

By analyzing the user's walk pattern in real time and correspondingly assisting the user in walking, the walking assistance device may properly assist the user in walking even when there is change in the user's walking habit or walking speed.

In addition, the controller 400 may include a change pattern analysis unit 420. In some example embodiments, the change pattern analysis unit 420 corrects the walking assistance time based on the pattern of change of the user's walk pattern. To analyze the pattern of change of the walk pattern, the change pattern analysis unit 420 may analyze correlations between plural walk patterns.

For example, in the case that the user's latest walk patterns are shortened more and more (e.g., in the case that the period of the walk cycle is shortened), the change pattern analysis unit 420 may assume that the user is accelerating and further shorten the calculated walking assistance time. In the case that latest walk patterns are elongated more and more (e.g., in the case that the period of the walk cycle is elongated), the change pattern analysis unit 420 may assume that the user is decelerating and further elongate the calculated walking assistance time.

The controller 400 may further include a torque adjustment unit 430. In some example embodiments, the torque adjustment unit 430 adjusts a pattern of torque to be produced by the walking assistance unit 100. The torque may follow a pattern of gradual increase and then gradual decrease. For example, the torque pattern may be the same as or similar to the pattern of energy necessary for the time of torque production as shown in FIG. 5, and may be preset to a form of a trapezoidal wave or a sinusoidal wave as shown in FIG. 7A.

More specifically, the torque adjustment unit 430 adjusts the torque pattern such that the walking assistance unit 100 assists the user's walking only for the calculated walking assistance time. At this time, the torque pattern may be adjusted based on various references. For example, the pattern may be adjusted based on the total amount of torque produced for the calculated walking assistance time. Alternatively, the pattern of produced torque may be adjusted by changing the rate of increase or decrease of torque based on the maximum value of the torque produced during the assistance period.

For example, referring to FIG. 7A, in the case that the total amount of torque produced in a trapezoidal pattern for the walking assistance time of the weight shift period P1 is 'A', and the total amount of torque produced in the walking assistance time of the mass shift period P2 is 'B', the torque adjustment unit 430 may adjust the torque production pattern such that a total torque (that may or may not be predetermined) is supplied in a trapezoidal pattern (that may or may not be predetermined), as shown in FIG. 7A.

In addition, in the case that torque needs to be produced in the form of a sinusoidal wave with a maximum value of 'a' for the walking assistance time of the weight shift period P1 and needs to be produced with a maximum value of 'b' for the walking assistance time of the mass shift period P2, the torque adjustment unit 430 may change the rate of increase or decrease of torque, adjusting the torque production pattern such that the maximum torque is produced for each walking assistance time, as shown in FIG. 7B.

In the case that a plurality of assistance periods is provided, the torque patterns for the respective assistance periods may differ from each other. For example, torque may be produced according to a pattern in a trapezoidal form in the weight shift period P1, and may be produced in a pattern in the form of a sinusoidal wave in the mass shift period P2.

FIG. 8 is a flowchart illustrating a method of controlling the walking assistance device according to some example embodiments.

Referring to FIG. 8, in operation S101, physical activities of a user occurring during walking are collected. In some example embodiments, physical activities refer to changes in the body occurring in the walk cycle such as contact of feet with the ground, cross of hip joints, and the period of the walk cycle.

For example, in operation S101, physical activities such as contact between the feet and the ground or hip joint cross may be collected by sensing change in pressure to the user's feet or based on a rotational angle of the walking assistance unit.

In operation S103, the walk pattern may be analyzed based on the collected physical activities. More specifically, the walk pattern may be analyzed by matching the physical activities collected in operation S101 and the time each of the physical activities has occurred to the walk cycle.

In operation S105, a walking assistance time is calculated according to the analyzed walk pattern. More specifically, the walking assistance time may be calculated using the time difference between the start time and termination time of the assistance period in the walk pattern.

For example, using the time difference between the time at which the heel of one leg contacts the ground and the time at which the hip joints cross each other, the walking assistance time of the weight shift period P1 may be calculated. In addition, using the time difference between the time at which the heel of the other leg contacts the ground and the time at which the hip joints cross each other, the walking assistance time of the mass shift period P2 may be calculated.

By analyzing the user's walk pattern in real time and correspondingly assisting the user in walking, the assisted walking device may properly assist the user in walking even when there is change in the user's walking habit or walking speed.

In operation S107, the walking assistance time may be corrected according to the pattern of change of the user's walk pattern. More specifically, in the case that the walk pattern is found to change in a certain pattern in analysis of correlations between last collected plural walk patterns, the length of the calculated walking assistance time may be corrected by reflecting the change pattern. By correcting the walking assistance time according to the change pattern of plural walk patterns, change in the user's walk speed may be estimated and thus the user may be assisted in walking.

In operation S109, a pattern of torque to be produced may be adjusted for the walking assistance time. Hereinafter, an example of adjustment of a torque pattern will be described with reference to FIG. 7B and Equation 1.

$$\tau = K \cdot \sin \omega t \qquad \text{Equation 1}$$

Equation 1 represents a pattern of torque gradually changing with time. In some example embodiments, '$\tau$' is a magnitude of torque produced at each time, '$K$' is a magnitude of the maximum torque, '$\omega$' is a variable to change the rate of increase or decrease in torque, and '$t$' is a variable representing change in time.

The torque produced during the assistance period may have a sinusoidal pattern as described in Equation 1. Accordingly, as time '$t$' passes, torque may gradually increase and then gradually decrease after reaching the maximum value.

The value of '$\omega$' is adjusted such that torque gradually increases from 0 and then gradually decreases to 0 to terminate the period after reaching the maximum value '$K$'. Accordingly, torque has a sharply changing pattern when the length of the period is shortened and has a smoothly changing pattern when the length of the period is extended.

In operation S111, when start of the assistance period is sensed, torque is produced according to the pattern of torque adjusted for the walking assistance time. At this time, torque in the pattern may gradually increase and then gradually decrease.

As is apparent from the above description, according to some example embodiments, walking may be efficiently assisted by providing torque according to a walk pattern only in an assistance period during which assisted walking is necessary.

In addition, feeling of difference caused to the user by the device may be minimized by analyzing the user's walk pattern through collection of the user's physical activities, calculating walking assistance time according to the analyzed walk pattern, and then assisting the user in walking only for the calculated walking assistance time.

Moreover, by correcting the walking assistance time based on the change pattern of the walk pattern, the device may promptly respond to the change in the user's walk speed.

In addition, battery power may be saved by providing torque only in the period during which a large amount of energy is necessary in a walk pattern of the walk cycle.

Finally, feeling of difference caused to the user by the device may be minimized by controlling torque for walking assistance such that torque gradually changes.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' means software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to wearable robots for humans and control methods thereof, those skilled in the art will appreciate that some example embodiments may be applied to other types of robots, systems, and control methods, such as wearable robots for animals and control methods thereof, or more general purpose systems and control methods.

While example embodiments have been particularly shown and described, it will be understood by those of ordinary skill in the art that various changes in form and details may be made therein without departing from the spirit and scope of the present invention as defined by the following claims.

What is claimed is:

1. A walking assistance device, comprising:
   a walking assistance unit configured to assist a user in walking;
   a plurality of sensors configured to sense change of pressure to a feet of the user and sense at least one of a rotational angle or a rotational rate of the walking assistance unit; and
   a controller configured to control the walking assistance unit to produce torque only in at least one assistance period needing walking assistance in a walk cycle based on a walk pattern of the user, the at least one assistance period being one or more portions of the walk cycle,
   wherein the controller is further configured to determine a first point in time of one foot of the user contacting a ground surface and a second point in time of hip joints of the user crossing each other subsequent to the first point in time, based on information from the plurality of sensors, and control the walking assistance unit to initiate to produce the torque at the first point in time and terminate production of the torque at the second point in time, and
   wherein the controller is further configured to determine a third point in time point of the other foot of the user contacting the ground surface and a fourth point in time of the hip joints of the user crossing each other subsequent to the third point in time, based on the information from the plurality of sensors, and control the walking assistance unit to initiate to produce the torque at the third point in time and terminate production of the torque at the fourth point in time.

2. The walking assistance device according to claim 1, wherein the controller is further configured to calculate a walking assistance time using a difference between a start time and termination time of the assistance period in the walk pattern, and
   wherein the controller is further configured to control the walking assistance unit to produce torque for the calculated walking assistance time in response to the assistance period starting.

3. The walking assistance device according to claim 2, wherein the controller comprises a pattern analysis unit configured to (1) analyze the walk pattern for a certain period of time to extract a change pattern of the walk pattern and (2) correct the walking assistance time based on the change pattern of the walk pattern.

4. The walking assistance device according to claim 2, wherein the controller comprises a torque adjustment unit configured to adjust a pattern of torque to be produced by the walking assistance unit, based on the walking assistance time.

5. The walking assistance device according to claim 1, wherein the torque is produced to gradually increase and then gradually decrease.

6. The walking assistance device according to claim 1, wherein the assistance period is a period in the walk cycle needing consumption of a relatively large amount of energy by the user.

7. The walking assistance device according to claim 1, wherein the at least one assistance period includes a plurality of assistance periods, and a torque pattern produced during one of the assistance periods differs from a torque pattern produced during another of the assistance periods.

8. The walking assistance device according to claim 1, further comprising:
   a status collector including the plurality of sensors and configured to collect a physical activity of the user,
   wherein the controller comprises a pattern analysis unit to analyze a walk pattern of the user based on the collected physical activity.

9. The walking assistance device according to claim 8, wherein the plurality of sensors comprise a pressure sensor configured to sense change in pressure applied to feet of the user.

10. The walking assistance device according to claim 8, wherein the plurality of sensors comprise an encoder sensor configured to collect information related to rotation of the walking assistance unit.

11. A method of controlling a walking assistance device, comprising:
    sensing change of pressure to a feet of a user and at least one of a rotational angle or a rotational rate of a walking assistance unit;
    calculating a walking assistance time using a difference between a start time and termination time of each of at least one assistance period needing walking assistance in a walk cycle, the at least one assistance period being one or more portions of the walk cycle; and
    assisting the user in walking, by producing torque only for the at least one walking assistance period,
    wherein the assisting includes,
    determining a first point in time of a heel of one foot of the user contacting a ground surface and a second point in time of hip joints of the user crossing each other subsequent to the first point in time, based on sensed information, and controlling the walking assistance unit to initiate to produce the torque at the first point in time and terminate production of the torque at the second point in time, and
    determining a third point in time point of a heel of the other foot of the user contacting the ground surface and a fourth point in time of the hip joints of the user crossing each other subsequent to the third point in time, based on the sensed information, and controlling the walking assistance unit to initiate to produce the torque at the third point in time and terminate production of the torque at the fourth point in time.

12. The method according to claim 11, further comprising:
    collecting physical activity information of the user; and analyzing a walk pattern of the user based on the collected physical activity information.

13. The method according to claim 11, wherein in the assisting, the torque is gradually changed.

14. The method according to claim 11, wherein the calculating comprises:
analyzing a walk pattern for a certain period of time to extract a change pattern of the walk pattern; and
correcting the calculated walking assistance time based on the change pattern of the walk pattern.

15. The method according to claim 11, wherein the assisting comprises adjusting a pattern of the torque based on the calculated walking assistance time.

16. The method according to claim 11, wherein the assisting comprises gradually increasing the torque and gradually decreasing the torque.

* * * * *